United States Patent [19]
Sato et al.

[11] Patent Number: 6,054,129
[45] Date of Patent: Apr. 25, 2000

[54] **FLAVOR-IMPROVED EXTRACT FROM *CASSIA MIMOSOIDES* L. VAR. *NOMAME* MAKINO AND METHOD OF PREPARING THE SAME**

[75] Inventors: Hiroshi Sato; Manabu Yamamoto, both of Saitama; Susumu Shimura, Tokyo, all of Japan

[73] Assignee: Lotte Co., Ltd., Tokyo, Japan

[21] Appl. No.: 09/210,726

[22] Filed: Dec. 15, 1998

[30] Foreign Application Priority Data

Dec. 16, 1997 [JP] Japan ..................... 9-346693

[51] Int. Cl.7 ............ A01N 65/00; A23L 1/226
[52] U.S. Cl. ............ 424/195.1; 426/533; 426/534; 426/650; 426/655
[58] Field of Search .......... 424/195.1; 426/533, 426/534, 650, 655

[56] References Cited

U.S. PATENT DOCUMENTS 5,674,498 10/1997 Inoue et al. ............... 424/195.1

OTHER PUBLICATIONS

Journ. Jap. Soc. Food Science & Tech. 1994 vol. 41 No. 8 pp. 561–564 (Partially translated), 1994.

Computer Abstract JICST–EPLUS AN 940726591 Susumu et al "Journ. Jap Soc. Food Sci & Tech." "Inhibitiory Effect of Tannin Fraction from *Cassia mimosoides*L. var. *noma-me*Makinop on Lipase Activity" (1994) vol. 41, No. 8 pp. 561–564, 1994.

Computer Abstract WPIDS 95–136830[18] JP07061981 (Mar. 7, 1995 "Novel tannin cpd. useful as food–aditive having lipase inhibitory activity".

*Primary Examiner*—Herbert J. Lilling
*Attorney, Agent, or Firm*—Young & Thompson

[57] ABSTRACT

A method includes preparing an extract from *Cassia mimosoides* L. var. *nomame* Makino subjecting *Cassia mimosoides* L. var. *nomame* Makino by extracting solvent to obtain an extract from *Cassia mimosoides* L. var. *nomame* Makino and roasting the extract, the extract being roasted to improve flavors.

32 Claims, No Drawings

FLAVOR-IMPROVED EXTRACT FROM *CASSIA MIMOSOIDES* L. VAR. *NOMAME* MAKINO AND METHOD OF PREPARING THE SAME

BACKGROUND OF THE INVENTION

The present invention relates to an extract from *Cassia mimosoides* L. var. *nomame* Makino, wherein the extract is capable of inhibiting a lipase activity and is remarkably reduced in astringency and bitterness as well as in unpleasant odor so that the extract is available for obesity-preventive agents and foods and drinks.

*Cassia mimosoides* L. var. *nomame* Makino is one of annual grasses classified into legume and has been drunken as a tea from long ago. Further, *Cassia mimosoides* L. var. *nomame* Makino has been used as civil-traditional medicines as a diuretic and stomachic.

In Japanese patent No. 2602387, it is disclosed that an extract extracted by a solvent from *Cassia mimosoides* L. var. *nomame* Makino is capable of inhibiting the activity of lipase which acts as a fats-digestive enzyme. In Japanese patent No. 2618202, it is disclosed that *Cassia mimosoides* L. var. *nomame* Makino is available as a hypo-lipid agent. In Japanese patent No. 2628832, it is disclosed that effective components of *Cassia mimosoides* L. var. *nomame* Makino for inhibiting the lipase activity are dimer of 3', 4', 7-trihydroxyflavan and catechin. In Japanese laid-open patent publication No. 8-259557, it is disclosed that flavan oligomers are condensed tannin specified to *Cassia mimosoides* L. var. *nomame* Makino.

Japanese patent No. 2602387 describes a method of extraction from *Cassia mimosoides* L. var. *nomame* Makino, wherein water or polarized or unpolarized organic solvent is used to obtain an extract from *Cassia mimosoides* L. var. *nomame* Makino. If this extract is added into foods, then the foods provide astringency and bitterness as well as unpleasant odors such as grass smell and musty smell. Japanese patent No. 2602387 describes that *Cassia mimosoides* L. var. *nomame* Makino is extracted by ethanol or ethanol solution to obtain a first extract so that the first extract is fractionated and refined by a column-chromatography to obtain a hypo-lipid agent. This method is, however, engaged with problem in its flavors.

In the above circumstances, it had been required to develop a flavor-improved extract from *Cassia mimosoides* L. var. *nomame* Makino, wherein the extract remains capable of inhibiting a lipase activity and is remarkably reduced in astringency and bitterness as well as in unpleasant odors of its own for availability to obesity-preventive agents and foods and drinks.

SUMMARY OF THE INVENTION

Accordingly, it is an object of the present invention to provide a novel extract from *Cassia mimosoides* L. var. *nomame* Makino free from the above problems.

It is a further object of the present invention to provide flavor-improved extract from *Cassia mimosoides* L. var. *nomame* Makino, wherein the extract remains capable of inhibiting a lipase activity and is remarkably reduced in astringency and bitterness as well as in unpleasant odors of its own for availability to obesity-preventive agents and foods and drinks.

It is a still further object of the present invention to provide a novel method of preparing a flavor-improved extract from *Cassia mimosoides* L. var. *nomame* Makino, wherein the extract remains capable of inhibiting a lipase activity and is remarkably reduced in astringency and bitterness as well as in unpleasant odors of its own for availability to obesity-preventive agents and foods and drinks.

It is yet a further object of the present invention to provide a novel obesity-preventive agent added with a flavor-improved extract from *Cassia mimosoides* L. var. *nomame* Makino.

It is a further more object of the present invention to provide novel foods and drinks added with a flavor-improved extract from *Cassia mimosoides* L. var. *nomame* Makino.

The present invention provides a method of preparing an extract from *Cassia mimosoides* L. var. *nomame* Makino. The method comprises the step of: subjecting *Cassia mimosoides* L. var. *nomame* Makino to an extracting solvent to obtain an extract from *Cassia mimosoides* L. var. *nomame* Makino; and roasting the extract.

The other present invention provides an extract from *Cassia mimosoides* L. var. *nomame* Makino, wherein the extract is roasted to improve flavors.

The above and other objects, features and advantages of the present invention will be apparent from the following descriptions.

DISCLOSURE OF THE INVENTION

The first present invention provides a method of preparing an extract from *Cassia mimosoides* L. var. *nomame* Makino. The method comprises the step of: subjecting *Cassia mimosoides* L. var. *nomame* Makino to an extracting solvent to obtain an extract from *Cassia mimosoides* L. var. *nomame* Makino; and roasting the extract.

It is preferable that the extract is roasted at a temperature in the range of 100–130° C. for 1–5 hours.

It is preferable to further comprise the steps of: subjecting the extract to a steam-distillation and a subsequent water-cleaning before the extract is roasted. It is further preferable that the extract is vacuum-concentrated at not less than 10 times for carrying out the steam-distillation with a steam amount of 1–5 times of the extract to remove a volatile component from the extract before a remainder of the extract is added with water at an amount of 5–100 times of the remainder for cleaning the extract.

The second present invention provides a method of preparing a base material for foods and drinks. The method comprising the steps of: subjecting *Cassia mimosoides* L var. *nomame* Makino to an extracting solvent to obtain an extract from *Cassia mimosoides* L. var. *nomame* Makino; roasting the extract; and adding a base material for foods and drinks.

It is preferable that the extract is roasted at a temperature in the range of 100–130° C. for 1–5 hours.

It is preferable to further comprise the steps of: subjecting the extract to a steam-distillation and a subsequent water-cleaning before the extract is roasted.

It is preferable that the extract is vacuum-concentrated at not less than 10 times for carrying out the steam-distillation with a steam amount of 1–5 times of the extract to remove a volatile component from the extract before a remainder of the extract is added with water at an amount of 5–100 times of the remainder for cleaning the extract.

The third present invention provides a method of preparing a base material for obesity-preventive agents. The method comprises the steps of: subjecting *Cassia mimosoides* L. var. *nomame* Makino to an extracting solvent to obtain an extract from *Cassia mimosoides L.* var. *nomame* Makino; roasting the extract; and adding a base material for obesity-preventive agents.

It is preferable that the extract is roasted at a temperature in the range of 100–130° C. for 1–5 hours.

It is preferable to further comprise the steps of: subjecting the extract to a steam-distillation and a subsequent water-cleaning before the extract is roasted. It is further preferable that the extract is vacuum-concentrated at not less than 10 times for carrying out the steam-distillation with a steam amount of 1–5 times of the extract to remove a volatile component from the extract before a remainder of the extract is added with water at an amount of 5–100 times of the remainder for cleaning the extract.

The fourth present invention provides a method of preparing a base material for hypo-lipid agents. The method comprises the steps of: subjecting *Cassia mimosoides L.* var. *nomame* Makino to an extracting solvent to obtain an extract from *Cassia mimosoides L.* var. *nomame* Makino; roasting the extract; and adding a base material for hypo-lipid agents.

It is preferable that the extract is roasted at a temperature in the range of 100–130° C. for 1–5 hours.

It is preferable to further comprise the steps of: subjecting the extract to a steam-distillation and a subsequent water-cleaning before the extract is roasted. It is further preferable that the extract is vacuum-concentrated at not less than 10 times for carrying out the steam-distillation with a steam amount of 1–5 times of the extract to remove a volatile component from the extract before a remainder of the extract is added with water at an amount of 5–100 times of the remainder for cleaning the extract.

The fifth present invention provides an extract from *Cassia mimosoides L.* var. *nomame* Makino, wherein the extract is roasted to improve flavors.

It is preferable that the extract is roasted at a temperature in the range of 100–130° C. for 1–5 hours.

It is also preferable that the extract is further subjected to a steam-distillation and a subsequent water-cleaning before the extract is roasted. It is further preferable that the extract is vacuum-concentrated at not less than 10 times for carrying out the steam-distillation with a steam amount of 1–5 times of the extract to remove a volatile component from the extract before a remainder of the extract is added with water at an amount of 5–100 times of the remainder for cleaning the extract.

The sixth present invention provides foods and drinks including an extract from *Cassia mimosoides L.* var. *nomame* Makino, wherein the extract is roasted to improve flavors.

It is preferable that the extract is roasted at a temperature in the range of 100–130° C. for 1–5 hours.

It is also preferable that the extract is further subjected to a steam-distillation and a subsequent water-cleaning before the extract is roasted. It is further preferable that the extract is vacuum-concentrated at not less than 10 times for carrying out the steam-distillation with a steam amount of 1–5 times of the extract to remove a volatile component from the extract before a remainder of the extract is added with water at an amount of 5–100 times of the remainder for cleaning the extract.

The seventh present invention provides an obesity-preventive agent including an extract from *Cassia mimosoides L.* var. *nomame* Makino, wherein the extract is roasted to improve flavors.

It is preferable that the extract is roasted at a temperature in the range of 100–130° C. for 1–5 hours.

It is also preferable that the extract is subjected to a steam-distillation and a subsequent water-cleaning before the extract is roasted. It is further preferable that the extract is vacuum-concentrated at not less than 10 times for carrying out the steam-distillation with a steam amount of 1–5 times of the extract to remove a volatile component from the extract before a remainder of the extract is added with water at an amount of 5–100 times of the remainder for cleaning the extract.

The eighth present invention provides a hypo-lipid agent including an extract from *Cassia mimosoides L.* var. *nomame* Makino, wherein the extract is roasted to improve flavors.

It is preferable that the extract is roasted at a temperature in the range of 100–130° C. for 1–5 hours.

It is also preferable that the extract is subjected to a steam-distillation and a subsequent water-cleaning before the extract is roasted. It is further preferable that the extract is vacuum-concentrated at not less than 10 times for carrying out the steam-distillation with a steam amount of 1–5 times of the extract to remove a volatile component from the extract before a remainder of the extract is added with water at an amount of 5–100 times of the remainder for cleaning the extract.

In accordance with the present invention, a fresh or dried above-ground part, preferably leaf or shell, of *Cassia mimosoides L.* var. *nomame* Makino as one of annual grasses classified into legume is crushed to be added with a three to ten times amount, preferably five times amount of water, a buffer solution or polarized or unpolarized solvent for extraction. Available extraction solvents are, for example, methanol, propanol, butanol, ether, hexane, chloroform, toluene, ethyl acetate, tetrahydrofuran and the like. Notwithstanding, it is unnecessary to limit the solvents to this list. It is possible to optionally select one or more kinds of those solvents for preparation. In consideration of the safety first, it is preferable to use ethanol, acetone, ethyl acetate. Particularly, ethanol used for drinks is more preferable. It is most preferable that ethanol is admixed with water, preferably at a ratio of 50% to 50%, for subsequent stirring the same at a temperature in the range of 20–70° C., preferably 60° C. for 30 minutes to 6 hours for extraction from *Cassia mimosoides L.* var. *nomame* Makino. It is also possible to subject remainders after extraction to re-extraction operations a few times.

The crushed *Cassia mimosoides L.* var. *nomame* Makino and the extraction solvent are put into a vessel with stirrer at a ratio in amount of 1 kg of the crushed *Cassia mimosoides L.* var. *nomame* Makino to 1–50 liters, preferably 5–10 liters, of the extraction solvent, before these are subjected to stirring operation for a predetermined time, for example, all day and night for subsequently gathering a filtrate. This filtrate is then subjected to a vacuum drying process (freeze-drying). In this case, a heated extraction solvent may be used. The obtained extract is light brown or brown paste or powder.

In order to obtain an extract reduced in astringency and bitterness as well as unpleasant odors, it is important to roast the extract or fractionated extract under conditions at a temperature of 100–130° C. for 1–5 hours, preferably at a temperature of 110° C. for 3 hours, whereby the extract is reduced in astringency and bitterness as well as unpleasant odors without reduction of lipase-inhibition activity.

In order to enhance the roasting effect, it is preferable that prior to the roasting process, the extract or fractionated extract is subjected to steam distillation and subsequent water-cleaning processes so that the extract is remarkably reduced in astringency and bitterness as well as unpleasant odors without reduction of lipase-inhibition activity. The steam distillation may be carried out by use of normally used system under normally selected conditions. Preferably, however, the extract after extraction is subjected to a vacuum concentration at 10 times or more and subsequent a distillation with 1–5 times amount, preferably 1.5 times amount of steam. A volatile constituent is removed from the extract by the steam distillation to obtain an extract remainder. The extract remainder is added with water for water-cleaning process. 5–100 times amount, preferably 10 times amount, of water is added to the extract remainder for stirring the same so that water-soluble components are moved into water to remove the water-soluble components from the extract remainder. Thereafter, the extract remainder is roasted to obtain the flavor-improved extract from *Cassia mimosoides L.* var. *nomame* Makino. The finally obtained extract from *Cassia mimosoides L.* var. *nomame* Makino is remarkably reduced in astringency and bitterness as well as unpleasant odors but is not reduced in lipase-inhibition activity.

In accordance with the present invention, about 30 g of the extract having the lipase-inhibition activity is obtained from 1 kg of branch-drawn *Cassia mimosoides L.* var. *nomame* Makino as raw materials. The trade name of the extract from *Cassia mimosoides L.* var. *nomame* Makino is Cassia polyphenol. Properties and components of the extract from *Cassia mimosoides L.* var. *nomame* Makino are shown on the following table 1.

TABLE 1

| Items | property and component |
|---|---|
| External appearance | powder |
| Color tone | brown |
| Flavors | flavors of its own free from unpleasant tastes and odors |
| Moisture | not more than 5% |
| Water-soluble component | not more than 10% |
| Polyphenol | not less than 45% |
| Condensed tannin | not less than 13% | where unpleasant tastes and odors are the astringency and bitterness as well as grass smell and musty smell, moisture is the moisture reduced by drying process.

The extract is directly roasted or roasted after the steam distillation and subsequent water-cleaning processes. The roasted extract may be filled into capsules or soft capsules. Alternatively, the roasted extract may also be formed in tablet type or granular type to be taken as the obesity-preventive agent. Further, alternatively, the roasted extract may also be mixed into materials for all foods and drinks, for example, various confectioneries such as chewing gums, chocolates, candies, tablets, biscuits, cookies, crackers and snacks, or various iced confectioneries such as ice creams and frozen confectioneries, various drinks such as soft drinks, nutrition drinks, cosmetic drinks and teas, and further breads, hams, soups, spaghettis and frozen foods. When the roasted extract is admixed into the materials for foods and drinks, the content of the roasted extract in the materials for foods and drinks may be adopted in consideration of the kinds of foods and drinks, shapes and intake amounts. In general, it is preferable to admix 0.02–80% of the roasted extract. In case of confectioneries, it is preferable to admix 0.2–10% of the roasted extract. In case of drinks, it is preferable to admix 0.02–1% of the roasted extract. In case of tablets, it is preferable to admix 2–80% of the roasted extract.

PREFERRED EMBODIMENTS

EXAMPLE 1

400 kg of powered and dried above-ground parts of *Cassia mimosoides L.* var. *nomame* Makino was added with 2000 liters of 50%-ethanol solution for subsequent stirring operation at 60° C. for 2 hours. A first remainder after a first filtration was added with 1500 liters of 50%-ethanol solution for subsequent stirring operation at 60° C. for 2 hours. A second remainder after a second filtration was added with 1500 liters of 50%-ethanol solution for subsequent stirring operation at 60° C. for 2 hours. The remainder of the extraction was removed by the above three times extractions with 5000 liters in total amount of water-containing ethanol. The extract free of the remainders was then subjected to a vacuum drying process to obtain about 40 kg of the extract.

It was confirmed that this dried extract has unpleasant odors such as grass smell and musty smell as well as astringency and bitterness, which is unsuitable for materials for foods and drinks.

The extract was placed in a torus-disk-roast apparatus to roast the extract at 130° C. for 2 hours. The effects of reductions in astringency and bitterness as well as unpleasant odors as well as the lipase-inhibition activity of the roasted extract were evaluated.

The roasted extract was subjected to a sensory evaluation by 10 panelists in comparison to unroasted extract to evaluate the astringency and bitterness as well as unpleasant odors. They provided plus 2-points if they could fee the roasted extract to be apparently improved. They provided plus 1-point if they could fee the roasted extract to be somewhat improved. They provided 0-point if they could fee the roasted extract to remain unchanged. They provided minus 1-point if they could fee the roasted extract to be somewhat deteriorated. They provided minus 2-points if they could fee the roasted extract to be apparently deteriorated. The maximum total point is plus 20 whilst the minimum total point is minus 20.

A measurement of the lipase-inhibition activity was made by measuring a fluorescence of fluorescent 4-methylumbelliferone in base material. Namely, 100 micro-liters of suspension containing 0.1 millimol of 4-methylumbelliferone oleate, 50 micro-liters of pig pancreatic lipase solution (McIlvaine buffer solution of pH 7.5, 45 micro-liters of a buffer solution and 5 micro-liters of either 50%-tetrahydrofuran or tetrahydrofuran solution at 50% of sample were put into a small test tube to cause a reaction at 37° C. for 20 minutes to form fluorescent 4-methylumbelliferone before 1 milliliter of 0.1 mol of hydrochloric acid was added into the small test tube to discontinue the reaction. 0.1 mol of sodium citrate solution was then added to adopt pH value of the solution into the vicinity of 4.3 before an intensity of fluorescence from the fluorescent 4-methylumbelliferone was measured by a fluorescence spectrophotometer at an excitation wavelength of 320 nanometers and a fluorescent wavelength of 450 nanometers. The lipase-inhibition activity is shown by the necessary amount $IC_{50}$ to be added for 50% reduction of the lipase activity.

TABLE 2

|  | unroast | roasted |
| --- | --- | --- |
| unpleasant odors | — | 12 points |
| astringency and bitterness | — | 8 points |
| $IC_{50}$ (μg) | 0.8 | 0.85 |
| relative activity | 100 | 94.1 | roast conditions: 130° C.; 2 hours

The above Table 2 shows that the roasted extract is reduced in astringency and bitterness as well as unpleasant odors with almost no reduction in relative activity of lipase-inhibition.

EXAMPLE 2

In order to confirm an optimum range of roast temperature, extracts from *Cassia mimosoides L.* var. *nomame* Makino by a water-containing ethanol were transferred into the torus-disk-roast apparatus to roast the extracts at various temperatures, for example, at 90° C., 100° C., 110° C., 120° C., 130° C., 140° C., 150° C., 160° C. and 170° C. for 2 hours. The roasted extracts were subjected to a sensory evaluation in comparison to unroasted extract to evaluate the astringency and bitterness as well as unpleasant odors as well as to a measurement of $IC_{50}$ as the lipase-inhibition activity. Results of sensory evaluation and $IC_{50}$-measurement are shown on the following Table 3.

TABLE 3

|  | unroast | roasted at 90° C. | roasted at 100° C. |
| --- | --- | --- | --- |
| unpleasant odors | — | 2 points | 15 points |
| astringency and bitterness | — | 4 points | 8 points |
| $IC_{50}$ (μg) | 0.8 | 0.8 | 0.8 |
| relative activity | 100 | 100 | 100 |

|  | roasted at 110° C. | roasted at 120° C. | roasted at 130° C. |
| --- | --- | --- | --- |
| unpleasant odors | 18 points | 16 points | 12 points |
| astringency and bitterness | 15 points | 13 points | 8 points |
| $IC_{50}$ (μg) | 0.81 | 0.83 | 0.85 |
| relative activity | 98.8 | 96.4 | 94.1 |

|  | roasted at 140° C. | roasted at 150° C. | roasted at 160° C. |
| --- | --- | --- | --- |
| unpleasant odors | 5 points | 5 points | −3 points |
| astringency and bitterness | 4 points | −7 points | −17 points |
| $IC_{50}$ (μg) | 1.07 | 2.67 | 4.21 |
| relative activity | 74.8 | 30.0 | 19.0 |

|  | roasted at 170° C. |
| --- | --- |
| unpleasant odors | −15 points |
| astringency and bitterness | −20 points |
| $IC_{50}$ (μg) | 10.67 |
| relative activity | 7.5 | roasted time: 2 hours.

The above Table 3 shows that the extracts roasted in the range of 100–130° C. are remarkably reduced in astringency and bitterness as well as unpleasant odors with almost no reduction in relative activity of lipase-inhibition. Then roast temperature of 110° C. is optimum to reduce the astringency and bitterness as well as unpleasant odors.

In order to further confirm an optimum range of roast time, extracts from *Cassia mimosoides L.* var. *nomame* Makino by a water-containing ethanol were transferred into the torus-disk-roast apparatus to roast the extracts at an optimum temperature of 110° C. for various times, for example, 15 minutes, 30 minutes, 1 hour, 2 hours, 3 hours, 4 hours, 5 hours, 6 hours and 9 hours. The roasted extracts were subjected to a sensory evaluation in comparison to unroasted extract to evaluate the astringency and bitterness as well as unpleasant odors as well as to a measurement of $IC_{50}$ as the lipase-inhibition activity. Results of sensory evaluation and $IC_{50}$-measurement are shown on the following Table 4.

TABLE 4

|  | unroast | roasted 15 min. | roasted 30 min. |
| --- | --- | --- | --- |
| unpleasant odors | — | 2 points | 5 points |
| astringency and bitterness | — | 0 point | 4 points |
| $IC_{50}$ (μg) | 0.8 | 0.8 | 0.8 |
| relative activity | 100 | 100 | 100 |

|  | roasted 1 hour | roasted 2 hours | roasted 3 hours |
| --- | --- | --- | --- |
| unpleasant odors | 12 points | 18 points | 18 points |
| astringency and bitterness | 10 points | 15 points | 19 points |
| $IC_{50}$ (μg) | 0.8 | 0.81 | 0.83 |
| relative activity | 100 | 98.8 | 96.4 |

|  | roasted 4 hours | roasted 5 hours | roasted 6 hours |
| --- | --- | --- | --- |
| unpleasant odors | 17 points | 12 points | 2 points |
| astringency and bitterness | 18 points | 11 points | 3 points |
| $IC_{50}$ (μg) | 0.85 | 0.87 | 1.07 |
| relative activity | 94.1 | 92.0 | 74.8 |

|  | roasted 9 hours |
| --- | --- |
| unpleasant odors | −6 points |
| astringency and bitterness | −9 points |
| $IC_{50}$ (μg) | 2.67 |
| relative activity | 30.0 | roasted temperature: 110° C.

The above Table 4 shows that the extracts roasted in the range of 1–5 hours are remarkably reduced in astringency and bitterness as well as unpleasant odors with almost no reduction in relative activity of lipase-inhibition.

EXAMPLE 3

In order to more effectively reduce the astringency and bitterness as well as unpleasant odors of the extract from *Cassia mimosoides L.* var. *nomame* Makino, steam distillation and subsequent water-cleaning processes were carried out.

400 kg of crushed branch-drawn *Cassia mimosoides L.* var. *nomame* Makino was added with 2000 liters of 50%-ethanol solution for subsequent stirring operation at 60° C. for 2 hours. A first remainder after a first filtration was added with 1500 liters of 50%-ethanol solution for subsequent stirring operation at 60° C. for 2 hours. A second remainder after a second filtration was added with 1500 liters of 50%-ethanol solution for subsequent stirring operation at 60° C. for 2 hours. The remainder of the extraction was removed by the above three times extractions with 5000 liters in total amount of water-containing ethanol. The extract free of the remainders was then condensed to about 400 liters (water-containing ethanol extract). This condensed solution was then transferred into a distillation kettle of 200 liters for a distillation for 2 hours with a steam at 2.0 kg/cm² and 300 liters per a hour in order to remove volatile components from the steam-distilled extract. The remainder was then added with 4000 liters of water of a temperature of not higher than 40° C. for stirring the same and subsequent leaving the same prior to removal of a supernatant liquid for the purpose of removing the liquid component from the extract. A precipitate was dried by vacuum freeze-dry to obtain a water-cleaned dry powered extract. This dry powered extract was then transferred into the torus-disk-roast apparatus to roast the extracts at a surface temperature of 110° C. for 3 hours, thereby obtaining 12.0 kg of the roasted extract. It was confirmed that this roasted extract is remarkably reduced in astringency and bitterness as well as unpleasant odors as compared to the above extracts in Examples 1 and 2 as well as that this roasted extract has an aromatic smelling which is suitable for the foods.

The flavors of the extracts in individual steps involved in the process for preparing the roasted extract form *Cassia mimosoides L.* var. *nomame* Makino are shown on the following Table 5, wherein astringency, bitterness and unpleasant odors are expressed in relative values to when unroasted extract is evaluated at 100.

TABLE 5

| Process | unpleasant odors | astringency | bitterness |
|---|---|---|---|
| plane extract | 100 | 100 | 100 |
| steam-distillated | 30 | 95 | 100 |
| water-cleaned | 20 | 50 | 20 |
| roasted | less than 5 | less than 10 | 5 | where plane extract is the water-containing ethanol extract.

Table 5 shows that as the sequential processes of the steam-distillation, water-cleaning and roasting are progressed, then the astringency, bitterness and unpleasant are improved.

The lipase-inhibition activity of the extracts in individual steps involved in the process for preparing the roasted extract form *Cassia mimosoides L.* var. *nomame* Makino are shown on the following Table 6, wherein $IC_{50}$ value, specific activity and total activity are shown.

TABLE 6

| Process | extract weight (kg)/ | $IC_{50}(\mu g)/$ | specific activity/ | total activity |
|---|---|---|---|---|
| plane extract | 40 | 0.8 | 1 | 40 |
| steam-distillated | 39.6 | 0.8 | 1 | 39.6 |
| water-cleaned | 12.3 | 0.27 | 2.96 | 36.4 |
| roasted | 11.3 | 0.28 | 2.86 | 34.0 | where specific activity is a ratio of $IC_{50}$ value of the water-containing ethanol extract to $IC_{50}$ value of the extract in individual steps, and the total activity is the product of the specific acidity and the extract weight.

Table 6 shows that as the sequential processes of the steam-distillation, water-cleaning and roasting are progressed, then the specific activity of the lipase-inhibition activity is improved whilst the yield is decreased. However no remarkable reduction in total activity appears as the sequential processes of the steam-distillation, water-cleaning and roasting are progressed.

EXAMPLE 4

3.5 kg of cacao mass, 1.5 kg of cacao butter, 0.45 kg of whole milk powder, 4.5 kg of sugar, and 20 g of the roasted extract obtained in Example 3 were put into a mixer for mixing at 38–43° C. for 30 minutes before the mixture was then transferred into a refiner for refining operation at 35–36° C. to obtain uniform particles of not larger than 40 micrometers in diameter. The particles were then transferred into a conching machine for conching process. Immediately before the conching process has been finished, 50 g of lecithin as an emulsifier and a small amount of essence were added for homogenization. A tempering is carried out at 27–32° C. for subsequent molding and cooling for solidification to obtain a chocolate. The chocolate has a good flavor and a capability of inhibiting lipase-activity.

EXAMPLE 5

500 g of gum base, 1.2 kg of sugar, 200 g of corn syrup, 20 g of softener/coloring, 20 g of citric acid, 10 g of essence, and 20 g of the roasted extract obtained in Example 3 were admixed to form a chewing gum. This chewing gum has a good flavor and a capability of inhibiting lipase-activity.

EXAMPLE 6

1 kg of wheat, 100 g of corn starch, 250 g of sugar, 125 g of margarine, 5 g of salt, 25 g of sodium carbonate, 8.8 g of ammonium carbonate, 6.3 g of soybean lecithin, 75 g of whole egg, 6.3 g vanilla oil and 15 g of the roasted extract obtained in Example 3 as well as 350 g of water were admixed to form a dough. The dough was gill-spread and then molded for roasted to form a biscuit. This biscuit has a good hardness and a capability of inhibiting lipase-activity.

EXAMPLE 7

150 g of sugar, 150 g of corn syrup, 60 g of condensed milk, 18.8 g of wheat, and 0.7 g of the roasted extract obtained in Example 3 were boiled at 120° C. before 2.2 g of butter, 1.6 g of cacao butter, 2.2 g of palm oil, 1 g of essence were farther added for stirring and subsequent cooling and molding to form a caramel. This caramel has a smooth-melting in mouth, a good flavor and a capability of inhibiting lipase-activity.

EXAMPLE 8

2.6 kg of 30%-fresh cream, 1.19 kg of skim condensed milk, 524 g of skim milk, 541 g of sugar, 720 g of corn syrup powder, 30 g of stabilizer, 4.32 kg of water, and 20 g of the roasted extract obtained in Example 3 were put into a mixer for mixing at 60–65° C. before the mixture was then transferred into a homogenizer for homogenization at 60–65° C. until fats become not larger than 2 micrometers to prepare an ice cream mix. This ice cream mix was then transferred into a bactericidal oven for placing the ice cream mix in the bactericidal oven at 85–90° C. for 15–30 seconds to sterilize the ice cream mix. The sterilized ice cream mix was then cooled at not higher than 5° C. for an aging and subsequent transfer of the ice cream mix into the freezer to freeze the same at −2° C. to −5° C. with mixing with air to form a soft ice cream. The soft ice cream was further frozen at −20° C. to form a hard ice cream. The soft and hard ice creams have a smooth-melting in mouth, a good flavor and a capability of inhibiting lipase-activity.

EXAMPLE 9

220 g of sugar, 168 g of corn syrup, 72 g of water were heated to be melt and then boiled at 145–150° C. Subsequently, 12 g of the roasted extract obtained in Example 3 were admixed to mold the same to form a hard candy. This hard candy has a smooth-melting in mouth, a good flavor and a capability of inhibiting lipase-activity.

EXAMPLE 10

1 liter of green tea was added with 0.2 g of the roasted extract obtained in Example 3 to prepare a hypo-lipidfunction enhanced green tea. The same to form a hard candy. This hard candy has a smooth-melting in mouth, a good flavor and a capability of inhibiting lipase-activity.

EXAMPLE 11

40 g of lactose, 19 g of corn starch, 15 g of the roasted extract obtained in Example 3 and 1 g of sugar ester were admixed and then extruded by an extruder-granulator for granulation before compression molding by punching machine to form 100 bare tablets of hypo-lipid agent A single tablet contains 150 mg of the extract.

EXAMPLE 12

100 g of sugar, 3 g of cyclodextrin, 1.5 g of sodium carbonate, 3 g of cellulose, 3 g of essence, 50 g of coffee extract, and 2 g of the roasted extract obtained in Example 3 were dissolved into water so that a total volume becomes 1000 milliliters for dividing the same into 50 milliliters to prepare a liquid medicine. This liquid medicine has a good flavor and a capability of inhibiting lipase-activity.

In accordance with the present invention, the roasted extract from *Cassia mimosoides L.* var. *nomame* Makino, wherein the roasted extract remains capable of inhibiting a lipase activity and is remarkably reduced in astringency and bitterness as well as in unpleasant odors of its own for availability to obesity-preventive agents and foods and drinks.

Whereas modifications of the present invention will be apparent to a person having ordinary skill in the art, to which the invention pertains, it is to be understood that embodiments as shown and described by way of illustrations are by no means intended to be considered in a limiting sense. Accordingly, it is to be intended to cover by claims all modifications which fall within the spirit and scope of the present invention.

What is claimed is:

1. A method of preparing an extract from *Cassia mimosoides L.* var. *nomame* Makino, said method comprising the step of:
    subjecting *Cassia mimosoides L.* var. *nomame* Makino to an extracting solvent to obtain an extract from *Cassia mimosoides L.* var. *nomame* Makino; and
    roasting said extract.

2. The method as claimed in claim 1, wherein said extract is roasted at a temperature in the range of 100–130° C. for 1–5 hours.

3. The method as claimed in claim 1, further comprising the steps of: subjecting said extract to a steam-distillation and a subsequent water-cleaning before said extract is roasted.

4. The method as claimed in claim 3, wherein said extract is vacuum-concentrated at not less than 10 times for carrying out said steam-distillation with a steam amount of 1–5 times of said extract to remove a volatile component from said extract before a remainder of said extract is added with water at an amount of 5–100 times of said remainder for cleaning said extract.

5. A method of preparing a base material for foods and drinks, said method comprising the steps of:
    subjecting *Cassia mimosoides L.* var. *nomame* Makino to an extracting solvent to obtain an extract from *Cassia mimosoides L.* var. *nomame* Makino;
    roasting said extract; and
    adding a base material for foods and drinks.

6. The method as claimed in claim 5, wherein said extract is roasted at a temperature in the range of 100–130° C. for 1–5 hours.

7. The method as claimed in claim 5, further comprising the steps of: subjecting said extract to a steam-distillation and a subsequent water-cleaning before said extract is roasted.

8. The method as claimed in claim 7, wherein said extract is vacuum-concentrated at not less than 10 times for carrying out said steam-distillation with a steam amount of 1–5 times of said extract to remove a volatile component from said extract before a remainder of said extract is added with water at an amount of 5–100 times of said remainder for cleaning said extract.

9. A method of preparing a base material for obesity-preventive agents, said method comprising the steps of:
    subjecting *Cassia mimosoides L.* var. *nomame* Makino to an extracting solvent to obtain an extract from *Cassia mimosoides L.* var. *nomame* Makino;
    roasting said extract; and
    adding a base material for obesity-preventive agents.

10. The method as claimed in claim 9, wherein said extract is roasted at a temperature in the range of 100–130° C. for 1–5 hours.

11. The method as claimed in claim 9, further comprising the steps of: subjecting said extract to a steam-distillation and a subsequent water-cleaning before said extract is roasted.

12. The method as claimed in claim 11, wherein said extract is vacuum-concentrated at not less than 10 times for carrying out said steam-distillation with a steam amount of 1–5 times of said extract to remove a volatile component from said extract before a remainder of said extract is added with water at an amount of 5–100 times of said remainder for cleaning said extract.

13. A method of preparing a base material for hypo-lipid agents, said method comprising the steps of:
    subjecting *Cassia mimosoides L.* var. *nomame* Makino to an extracting solvent to obtain an extract from *Cassia mimosoides L.* var. *nomame* Makino;
    roasting said extract; and
    adding a base material for hypo-lipid agents.

14. The method as claimed in claim 13, wherein said extract is roasted at a temperature in the range of 100–130° C. for 1–5 hours.

15. The method as claimed in claim 13, further comprising the steps of: subjecting said extract to a steam-distillation and a subsequent water-cleaning before said extract is roasted.

16. The method as claimed in claim 15, wherein said extract is vacuum-concentrated at not less than 10 times for carrying out said steam-distillation with a steam amount of 1–5 times of said extract to remove a volatile component from said extract before a remainder of said extract is added with water at an amount of 5–100 times of said remainder for cleaning said extract.

17. An extract from *Cassia mimosoides L.* var. *nomame* Makino, wherein said extract is roasted to improve flavors.

18. The extract as claimed in claim 17, wherein said extract is roasted at a temperature in the range of 100–130° C. for 1–5 hours.

19. The extract as claimed in claim 17, wherein said extract is further subjected to a steam-distillation and a subsequent water-cleaning before said extract is roasted.

20. The extract as claimed in claim 19, wherein said extract is vacuum-concentrated at not less than 10 times for carrying out said steam-distillation with a steam amount of 1–5 times of said extract to remove a volatile component from said extract before a remainder of said extract is added with water at an amount of 5–100 times of said remainder for cleaning said extract.

21. Foods and drinks including an extract from *Cassia mimosoides L.* var. *nomame* Makino, wherein said extract is roasted to improve flavors.

22. The foods and drinks as claimed in claim 21, wherein said extract is roasted at a temperature in the range of 100–130° C. for 1–5 hours.

23. The foods and drinks as claimed in claim 21, wherein said extract is further subjected to a steam-distillation and a subsequent water-cleaning before said extract is roasted.

24. The foods and drinks as claimed in claim 23, wherein said extract is vacuum-concentrated at not less than 10 times for carrying out said steam-distillation with a steam amount of 1–5 times of said extract to remove a volatile component from said extract before a remainder of said extract is added with water at an amount of 5–100 times of said remainder for cleaning said extract.

25. An obesity-preventive agent including an extract from *Cassia mimosoides L.* var. *nomame* Makino, wherein said extract is roasted to improve flavors.

26. The obesity-preventive agent as claimed in claim 25, wherein said extract is roasted at a temperature in the range of 100–130° C. for 1–5 hours.

27. The obesity-preventive agent as claimed in claim 25, wherein said extract is subjected to a steam-distillation and a subsequent water-cleaning before said extract is roasted.

28. The obesity-preventive agent as claimed in claim 27, wherein said extract is vacuum-concentrated at not less than 10 times for carrying out said steam-distillation with a steam amount of 1–5 times of said extract to remove a volatile component from said extract before a remainder of said extract is added with water at an amount of 5–100 times of said remainder for cleaning said extract.

29. A hypo-lipid agent including an extract from *Cassia mimosoides L.* var. *nomame* Makino, wherein said extract is roasted to improve flavors.

30. The hypo-lipid agent as claimed in claim 29, wherein said extract is roasted at a temperature in the range of 100–130° C. for 1–5 hours.

31. The hypo-lipid agent as claimed in claim 29, wherein said extract is subjected to a steam-distillation and a subsequent water-cleaning before said extract is roasted.

32. The hypo-lipid agent as claimed in claim 31, wherein said extract is vacuum-concentrated at not less than 10 times for carrying out said steam-distillation with a steam amount of 1–5 times of said extract to remove a volatile component from said extract before a remainder of said extract is added with water at an amount of 5–100 times of said remainder for cleaning said extract.

* * * * *

UNITED STATES PATENT AND TRADEMARK OFFICE
CERTIFICATE OF CORRECTION

PATENT NO.   : 6,054,129
DATED        : April 25, 2000
INVENTOR(S)  : Hiroshi Sato et al.

It is certified that error appears in the above-identified patent and that said Letters Patent is hereby corrected as shown below:

Claim 1,
Line 4, change "an" (second occurrence) to -- dried --;
Line 6, after "said" insert -- dried --.

Claim 5,
Line 4, change "an" to -- a dried --;
Line 6, after "said" insert -- dried --.

Claim 9,
Line 4, change "an" (second occurrence) to -- a dried --;
Line 6, after "said" insert -- dried --.

Claim 13,
Line 4, change "an" (second occurrence) to -- a dried --;
Line 6, after "said" insert -- dried --.

Claim 17,
Line 1, change "An" to -- A dried --;
Line 2, after "said" insert -- dried --.

UNITED STATES PATENT AND TRADEMARK OFFICE
CERTIFICATE OF CORRECTION

PATENT NO. : 6,054,129
DATED : April 25, 2000
INVENTOR(S) : Hiroshi Sato et al.

It is certified that error appears in the above-identified patent and that said Letters Patent is hereby corrected as shown below:

Claim 21,
Line 1, change "an" to -- a dried --;
Line 3, after "said" insert -- dried --.

Claim 25,
Line 1, change "an" to -- a dried --;
Line 3, after "said" insert -- dried --.

Claim 29,
Line 1 change "an" to -- a dried --;
Line 3, after "said" insert -- dried --.

Signed and Sealed this

Seventh Day of August, 2001

*Attest:*

*Nicholas P. Godici*

*Attesting Officer*

NICHOLAS P. GODICI
*Acting Director of the United States Patent and Trademark Office*